(12) United States Patent
Saka et al.

(10) Patent No.: US 7,123,004 B2
(45) Date of Patent: Oct. 17, 2006

(54) METHOD OF NON-DESTRUCTIVE INSPECTION OF REAR SURFACE FLAWS AND MATERIAL CHARACTERISTICS USING ELECTROMAGNETIC TECHNIQUE AND APPARATUS THEREFOR

(75) Inventors: Masumi Saka, Sendai (JP); Hironori Tomyo, Sendai (JP); Yasuko Saito, Sendai (JP)

(73) Assignee: Tohoku Techno Arch Co., Ltd., (JP)

( * ) Notice: Subject to any disclaimer, the term of this patent is extended or adjusted under 35 U.S.C. 154(b) by 0 days.

(21) Appl. No.: 10/959,236

(22) Filed: Oct. 6, 2004

(65) Prior Publication Data
US 2005/0212514 A1    Sep. 29, 2005

(30) Foreign Application Priority Data
Mar. 25, 2004    (JP) .............................. 2004-088548

(51) Int. Cl.
*G01N 27/82* (2006.01)
(52) U.S. Cl. ...................................... 324/238; 324/224
(58) Field of Classification Search ................ 324/224, 324/238
See application file for complete search history.

(56) References Cited

U.S. PATENT DOCUMENTS 3,020,745 A * 2/1962 Sielicki .......................... 374/5
4,872,762 A * 10/1989 Koshihara et al. ............. 374/5

FOREIGN PATENT DOCUMENTS

JP    2004-88548    12/2004

* cited by examiner

*Primary Examiner*—Reena Aurora
(74) *Attorney, Agent, or Firm*—Hayes Soloway P.C.

(57) ABSTRACT

The non-destructive inspection method, wherein the non-destructive inspection method supplies currents to a conductive inspection subject and evaluates the rear surface flaw and the embedded flaw of these the inspection subject, or the material characteristic using a DC electric potential method, and an inspection sensitivity to the rear surface flaw, the embedded flaw, or the material characteristic is increased by changing the electric resistivity distribution inside the inspection subject by locally heating a front surface of the inspection subject, thereby increasing an electric resistivity of the front surface of the inspection subject compared with an electric resistivity of the rear surface thereof, resulting in increasing currents supplied on a rear surface side compared with a case without the front surface being heated.

4 Claims, 4 Drawing Sheets

METHOD OF NON-DESTRUCTIVE INSPECTION OF REAR SURFACE FLAWS AND MATERIAL CHARACTERISTICS USING ELECTROMAGNETIC TECHNIQUE AND APPARATUS THEREFOR

BACKGROUND OF THE INVENTION

1. Field of the Invention

The present invention relates to a method and an apparatus which, in a non-destructive inspection method for evaluating rear surface flaws, embedded flaws, or material characteristics using an electromagnetic technique, increase an inspection sensitivity to the rear surface flaws, the embedded flaws, or the material characteristics by locally heating a front surface of an inspection subject, thereby increasing currents supplied on a rear surface side of the inspection subject. The present invention particularly relates to a preferred technique for carrying out a non-destructive inspection with a high sensitivity to rear surface flaws, embedded flaws, or material characteristics when an inspection subject is a thick member.

2. Description of the Related Art

With a background that flaw acceptance criteria and damage tolerance designs are correspondingly applied to structures such as a nuclear plant, there is required a non-destructive inspection method providing a high flaw detection capability and evaluating shapes of flaws. On the other hand, these structures are often constructed using thick members, and it is difficult to detect rear surface flaws and embedded flaws of these thick members using generally available non-destructive inspection methods using electromagnetic techniques.

Conventionally, as one of the non-destructive inspection methods using the electromagnetic techniques, there is known a potential difference method which non-destructively inspects flaws or material characteristics by supplying currents to a conductive inspection subject, and then measuring an electric potential difference on a front surface of the inspection subject. The potential difference method includes methods using an AC source and a DC source as a current source thereof, which are respectively referred to as the AC potential difference method, and the DC potential difference method. If an AC with a high frequency is used, most currents flow along a front surface (skin effect), and the AC potential difference method is thus not suitable for flaw detection on a rear surface side of an inspection subject. On the other hand, in the DC potential difference method, DC currents flow through an inside as well as along a front surface of an inspection subject, and a current field is thus disturbed by embedded flaws and rear surface flaws in addition to front surface flaws. Consequently, a non-destructive inspection can be carried out for the above flaws by measuring the disturbances as changes in the electric potential difference on the front surface of the inspection subject. However, if an inspection subject is a thick member, only weak DC currents are supplied on the rear surface side of the inspection subject, and there is such a problem that a detection sensitivity to flaws on the rear surface remarkably decreases.

On the other hand, an eddy current flaw detection method is known as a non-destructive inspection method using the electromagnetic technique. According to the eddy current flaw detection method, a coil to which an AC is supplied is placed in contact with or with a narrow gap to a top of a conductive inspection subject, and eddy currents are induced on the inspection subject due to an electromagnetic induction phenomenon. If a flaw is present in the inspection subject, changes in the eddy currents caused by the flaw are detected as a change in the impedance of the coil. Though the eddy current flaw detection method presents an excellent sensitivity to front surface flaws in principle, the skin effect attenuates the eddy currents in the thickness direction, and thus the method is not suitable for flaw detection on a rear surface side of an inspection subject, and the application thereof is conventionally limited to front surface flaw detection, and thin plate flaw detection.

In addition, the electric potential difference on the front surface of the inspection subject and the impedance of the coil measured by the above-described electromagnetic techniques correlate to physical properties of a material such as an electric conductivity, a magnetic permeability, and a film thickness, these physical properties of the material in a range as far as the currents flow are thus non-destructively inspected using the electromagnetic techniques. However, if an inspection subject is a thick member, currents supplied on a rear surface side are weak, and it is thus extremely difficult to detect changes in a material on the rear surface.

As described above, according to the conventional electromagnetic techniques, only weak currents are supplied on a rear surface side of an inspection subject, and it is thus difficult to detect rear surface flaws, embedded flaws, and material properties of a thick member.

SUMMARY OF THE INVENTION

The present inventors have strenuously carried out research for increasing the detection sensitivity to flaws on a rear surface side or the material properties of a thick member using electromagnetic techniques. As a result, there is obtained a technical knowledge that, advantageously utilizing a physical phenomenon that electric resistivity changes in a conductive inspection subject according to temperature, in the DC potential difference method, a front surface of the inspection subject is locally heated so as to form such an electric resistivity distribution that an electric resistivity on the front surface of the inspection subject is larger than the electric resistivity on the rear surface in the inspection subject, and consequently, more DC currents are supplied on the rear surface side compared with a case without the front surface being heated. There is also obtained a knowledge that, in the AC potential difference method and the eddy current flaw detection method, where the skin effect poses the problem, a penetration depth δ of the AC currents to an inspection subject is generally expressed by a following equation 1 (f[Hz]: AC frequency, μ [H/m]: magnetic permeability of the inspection subject, and σ [S/m]: electric conductivity of the inspection subject), and heating a front surface so as to increase an electric resistivity thereof thus decreases the electric conductivity σ (reciprocal of the electric resistivity), and increases the penetration depth δ accordingly. The present inventors have realized a non-destructive inspection method which, even if an inspection subject is a thick member, highly sensitively detects flaws on a rear surface side or material characteristics thereof based on the above technical knowledge.

$$\delta = \frac{1}{\sqrt{\pi f \mu \sigma}} \qquad \text{[Equation 1]}$$

According to a first aspect of the present invention, there is provided a non-destructive inspection method for evaluating rear surface flaws, embedded flaws, or material characteristics using an electromagnetic technique, where an electromagnetic physical quantity is measured while an electric resistivity distribution inside an inspection subject is changed by heating, cooling, or heating and cooling the inspection subject.

The first aspect provides a non-destructive inspection method using the electromagnetic technique to evaluate the rear surface flaws, the embedded flaws, and the material characteristics, and a principal characteristic thereof is to utilize the physical phenomenon that the electric resistivity of the inspection subject changes according to a temperature thereof, thus to generate an intended temperature distribution inside the inspection subject, thereby changing the electric resistivity distribution, and consequently to control a current density distribution in the inspection subject.

According to a second aspect of the present invention, there is provided the non-destructive inspection method according to the first aspect, where the non-destructive inspection method evaluates the rear surface flaws, the embedded flaws, or the material characteristics using a DC potential difference method, and an inspection sensitivity to the rear surface flaws, the embedded flaws, or the material characteristics is increased by changing the electric resistivity distribution inside the inspection subject by locally heating a front surface of the inspection subject, thereby increasing an electric resistivity of the front surface of the inspection subject compared with an electric resistivity of the rear surface thereof, resulting in increasing currents supplied on the rear surface side compared with a case without the front surface being heated.

The second aspect uses the DC potential difference method as the electromagnetic technique, and changes the electric resistivity distribution inside the inspection subject by locally heating the front surface of the inspection subject. In the inspection subject is formed such an electric resistivity distribution that the electric resistivity on the front surface of the inspection subject is larger than the electric resistivity on the rear surface thereof, and more DC currents are thus supplied on the rear surface side compared with a case without the front surface being heated, thereby increasing the detection sensitivity to the rear surface flaws, the embedded flaws, and the material characteristics.

According to a third aspect of the present invention, there is provided a non-destructive inspection apparatus, including a sensor including a mechanism which brings electric current input/output terminals connected to a constant current source, and electric potential difference measuring terminals in uniform contact with a front surface of an inspection subject, and a heat source for locally heating the front surface of the inspection subject, thereby changing an electric resistivity distribution inside the inspection subject, where rear surface flaws, embedded flaws, or material characteristics are inspected based on a measured electric potential difference.

According to the method of the present invention, more currents are supplied to a rear surface of an inspection subject in an electromagnetic technique, thereby enabling a non-destructive inspection with a higher sensitivity to rear surface flaws, embedded flaws, or material characteristics.

DETAILED DESCRIPTION OF THE PREFERRED EMBODIMENTS

WORKING EXAMPLE 1

Figure 1:
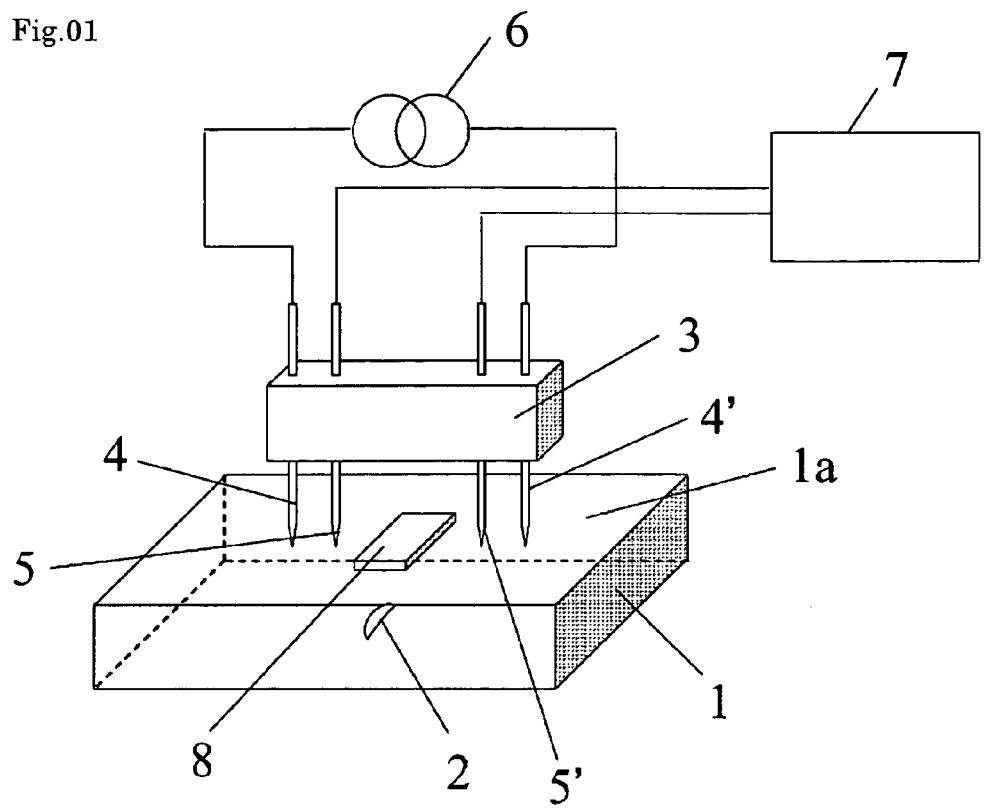
FIG. 1 is a conceptual drawing showing a non-destructive inspection method of rear surface flaws, and material characteristics using an electromagnetic technique according to the present invention.
Figure 2:
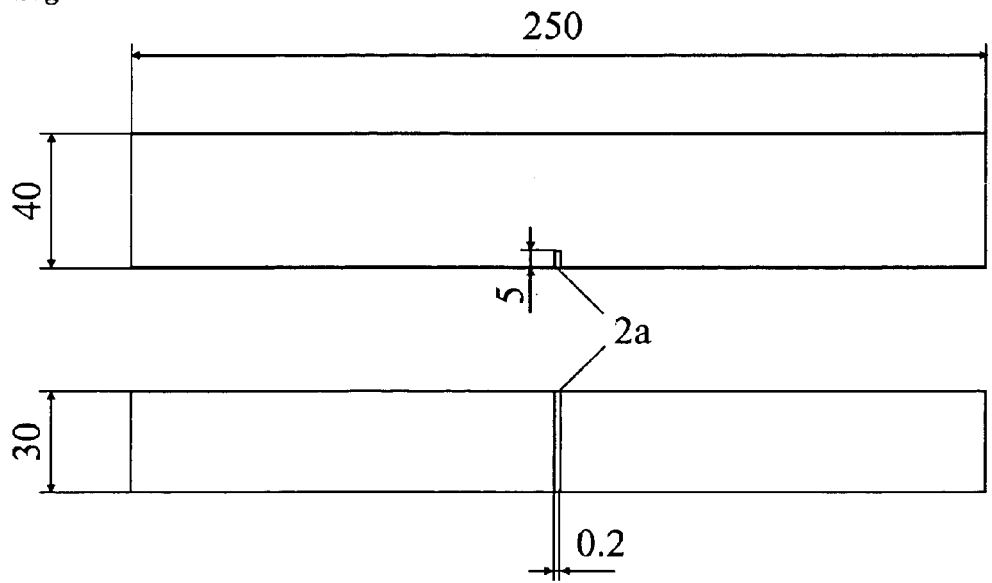
FIG. 2 describes shapes and dimensions of flaw inspection subjects used as a working example 1 and a reference example 1.

A description will now be given of working examples of a non-destructive inspection method of rear surface flaws and material characteristics using an electromagnetic technique while a DC potential difference method is selected as the electromagnetic technique, but the present invention is not limited to these working examples. FIG. 1 shows a constitution example of a non-destructive inspection method of the rear surface flaws and material characteristics using the electromagnetic technique. In FIG. 1, though a heat source 8 for heating, cooling, or a combination thereof is placed in contact with a front surface of an inspection subject, constitutions of the heat source 8 such as a placement, and a contact/non-contact state do not make a difference. As an inspection subject 1 of the present working example, there is used a stainless steel (AISI304) plate with exterior dimensions of 250 mm×30 mm, and a thickness of 40 mm shown in FIG. 2, and an artificial slit 2a with a depth of 5 mm, and a width of 0.2 mm is formed on a rear surface as a rear surface flaw 2 by electric discharge machining. Both electric current input/output terminals 4, 4' (separated from each other by 120 mm), and electric potential difference measuring terminals 5, 5' (separated from each other by 40 mm) are arranged symmetrical with respect to the flaw, and a spring mechanism in a probe 3 causes the terminals to be in vertical and uniform contact with an inspection subject front surface 1a. As the heat source 8 for heating, cooling, or a combination thereof, there is used a nichrome heater with exterior dimensions of 10 mm×30 mm. A DC current of 10 A is supplied from a DC constant current source 6 to the inspection subject 1 while the inspection subject front surface 1a is heated by the heater, and an electric potential difference measuring unit 7 measures an electric potential difference of the inspection subject front surface. There is also used an inspection subject with the same material and shape as the inspection subject 1 except for the flaw, and an electric potential difference is measured on the inspection subject front surface while the inspection subject front surface 1a is heated. Then, there is obtained a difference between the electric potential difference at a location with the rear surface flaw 2 and the electric potential difference at a location without the rear surface flaw 2 (Δ electric potential difference=|electric potential difference at location with flaw−electric potential difference at location without flaw|).

Figure 3:
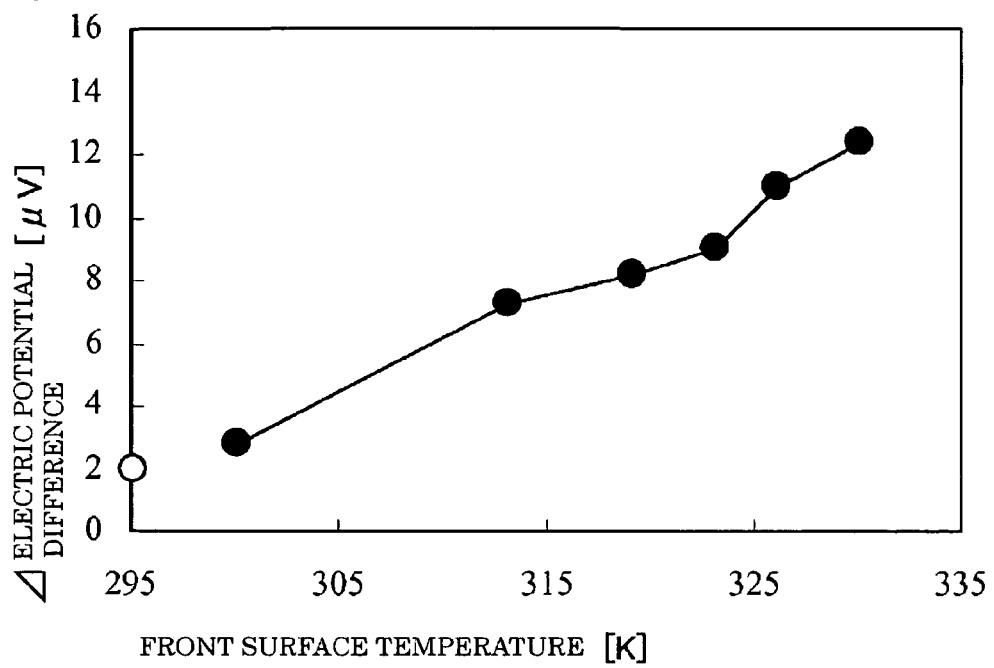
FIG. 3 shows differences between an electric potential difference at a location with a rear surface flaw in the working example 1 and an electric potential difference at a location without the rear surface flaw in the reference example 1.

In FIG. 3, black filled dots and solid lines show a change in the Δ electric potential difference with respect to a front surface temperature of the inspection subjects in the working example 1, and a hollow dot (reference example 1) shows the Δ electric potential difference if the inspection subject front surfaces 1a are not heated (at a room temperature of 295 K). In FIG. 3, while the Δ electric potential difference is 2 μV, which is small, when the inspection subject front surfaces 1a are not heated, the Δ electric potential difference has significantly increased to 12 μV at 335 K (reached in 10 minutes from a start of heating). It can be observed that the non-destructive inspection method of rear surface flaws and material characteristics using the electromagnetic technique according to the present invention increases a detection sensitivity to rear surface flaws.

WORKING EXAMPLE 2

Figure 4:
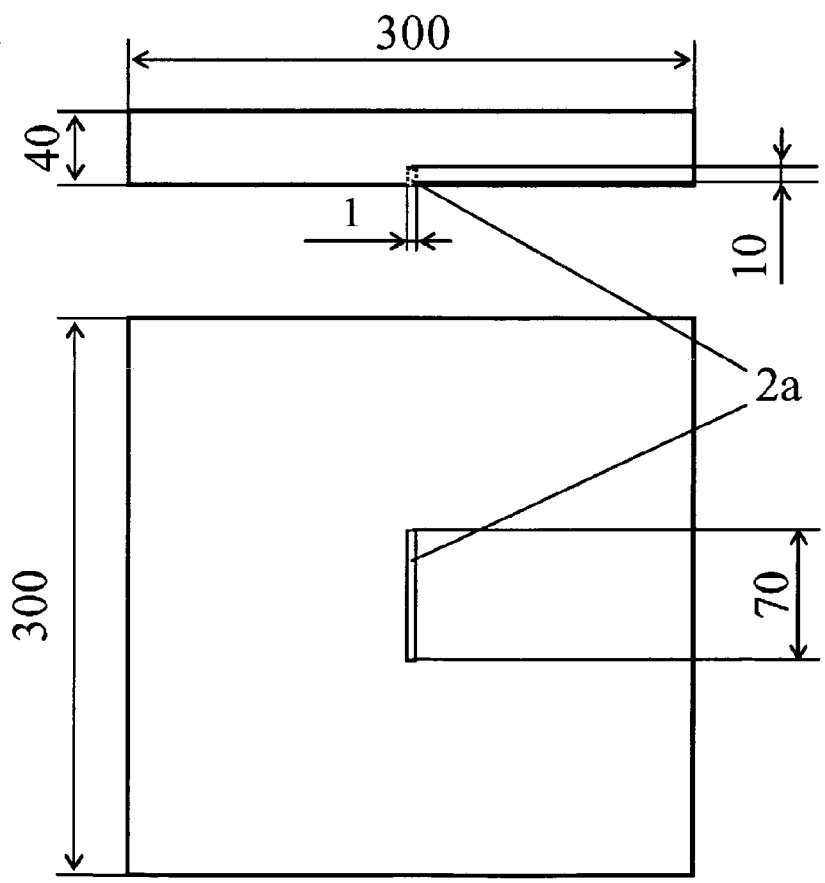
FIG. 4 describes shapes and dimensions of flaw inspection subjects used as a working example 2 and a reference example 2.

As an inspection subject 1 of a working example 2, there is used a stainless steel (AISI304) plate with exterior dimensions of 300 mm×300 mm, and a thickness of 40 mm shown in FIG. 4, and an artificial slit 2a with a length of 70 mm, a depth of 10 mm, and a width of 1 mm is formed on a rear surface as a rear surface flaw 2 by cutting. Electric current input/output terminals 4, 4' are separated from each other by 90 mm, and electric potential difference measuring terminals 5, 5' are separated from each other by 70 mm. As the heat source 8 for heating, cooling, or a combination thereof, there is used a ceramic heater with exterior dimensions of 20 mm×20 mm. A DC current of 15 A is used, and electric potential differences at a location with the flaw and at a location without the flaw are measured as in the working example 1, and then, a difference between both of the electric potential differences (Δelectric potential difference=|electric potential difference at location with flaw−electric potential difference at location without flaw|) is obtained.

Figure 5:
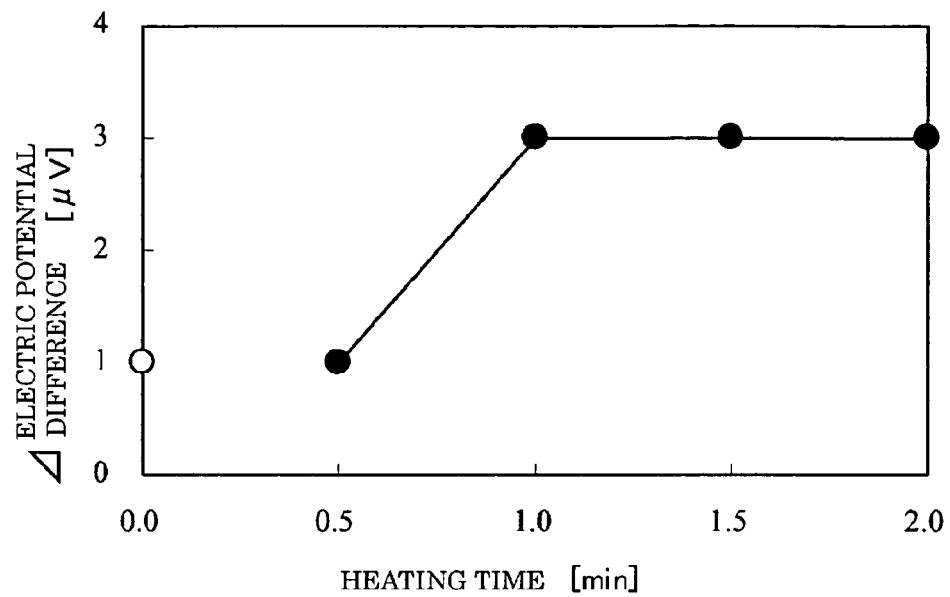
FIG. 5 shows differences between an electric potential difference at a location with a rear surface flaw in the working example 2 and an electric potential difference at a location without the rear surface flaw in the reference example 2.

In FIG. 5, black filled dots and solid lines show a change in the Δ electric potential difference with respect to a heating time in the working example 2, and a hollow dot (reference example 2) shows the Δ electric potential difference if the inspection subject front surfaces 1a are not heated (at a room temperature of 295 K). In FIG. 5, while the Δ electric potential difference is about 1 μV when the inspection subject front surfaces are not heated, the Δ electric potential difference increases to about 3 μV in one minute from a start of heating in the non-destructive inspection method of rear surface flaws and material characteristics using the electromagnetic technique according to the present invention. It can be observed that the detection sensitivity to rear surface flaws increases.

WORKING EXAMPLE 3

Figure 6:
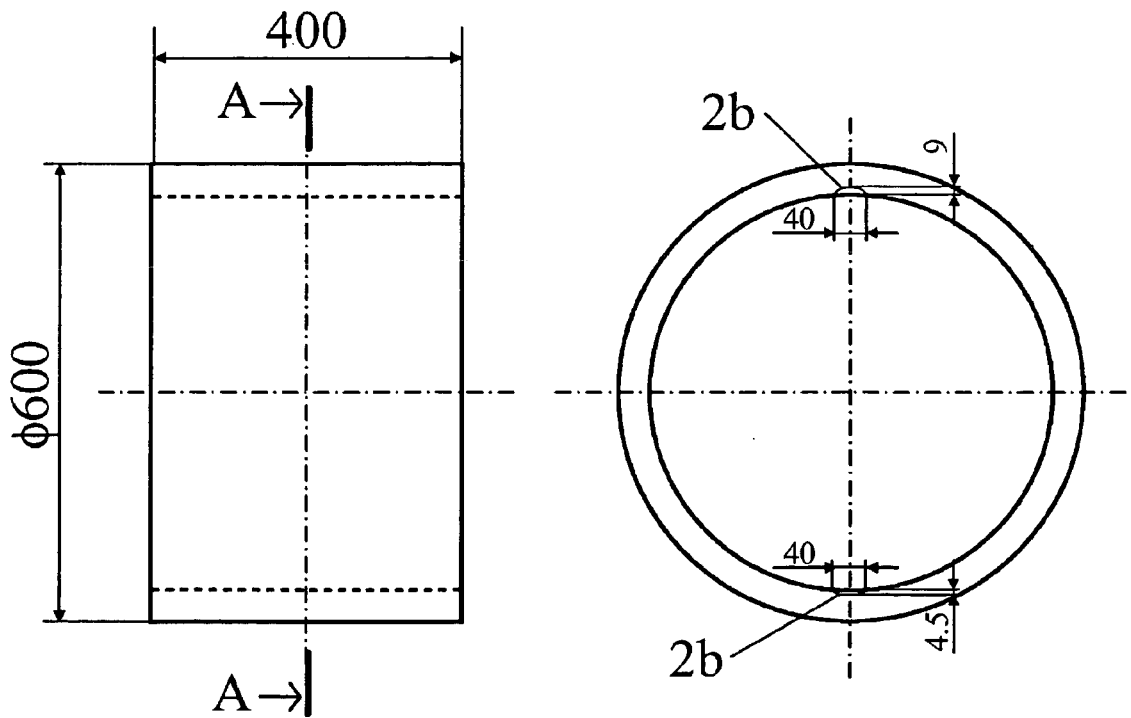
FIG. 6 describes shapes and dimensions of flaw inspection subjects used as a working example 3 and a reference example 3.

In a working example 3, an inspection subject 1 is a stainless steel pipe with a diameter of 600 mm, a thickness of 40 mm, and a length of 400 mm appearing in FIG. 6. On an inner wall of the pipe are formed two types of artificial notches 2b with respective depths of 9 mm and 4.5 mm and the same length of 40 mm by electric discharge machining. Electric current input/output terminals 4, 4' are separated from each other by 90 mm, and electric potential difference measuring terminals 5, 5' are separated from each other by 50 mm. Electric potential differences at a location with the flaw and at a location without the flaw are measured as in the working example 2, and then, a difference between both of the electric potential differences (Δ electric potential difference=| electric potential difference at location with flaw−electric potential difference at location without flaw|).

Figure 7:
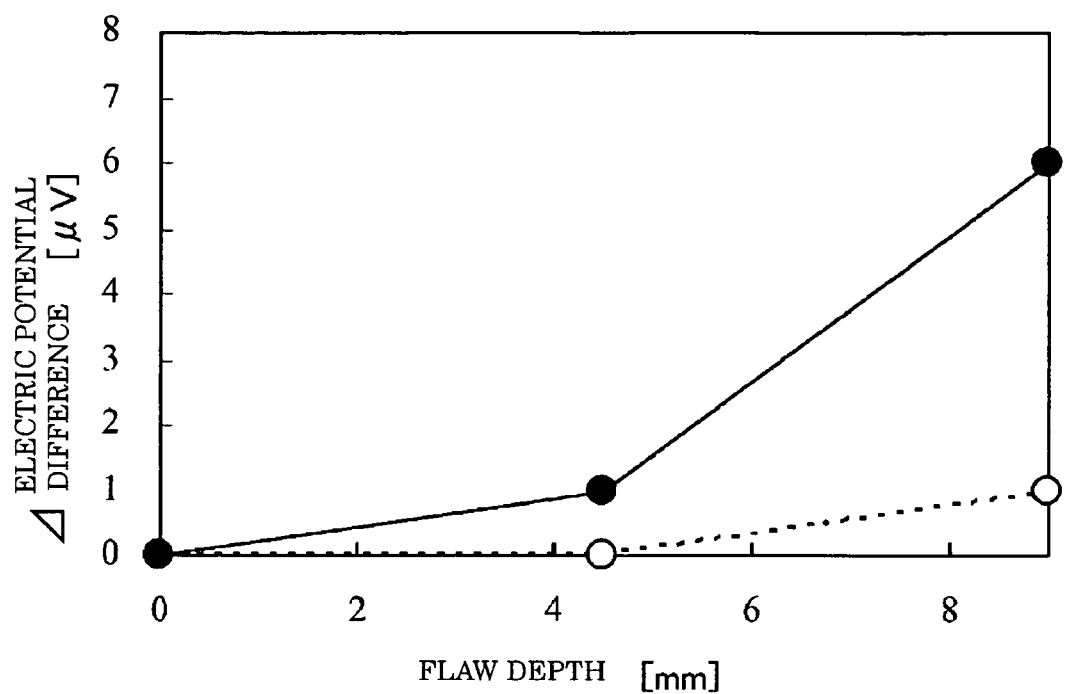
FIG. 7 shows differences between an electric potential difference at a location with a rear surface flaw in the working example 3 and an electric potential difference at a location without the rear surface flaw in the reference example 3.

In FIG. 7, black filled dots and solid lines show changes in the Δ electric potential difference with respect to the flaw depth at an inspection subject front surface temperature of 373 K (reached in about five minutes from a start of heating at both of the locations) in the working example 3, and hollow dots and dotted lines (reference example 3) show changes in the Δ electric potential difference if the inspection subject front surfaces 1a are not heated. In FIG. 7, while the Δ electric potential differences corresponding to the flaw depths of 4.5 and 9 mm are about 0 and 1 μV respectively when the inspection subject front surfaces 1a are not heated, the Δ electric potential differences have increased to about 1 and 6 μV in the non-destructive inspection method of rear surface flaws and material characteristics using the electromagnetic technique according to the present invention. It can be thus observed that the detection sensitivity to rear surface flaws increases.

What is claimed is:

1. A non-destructive inspection method for evaluation of a rear surface flaw, an embedded flaw, or a material characteristic of a workpiece using an electromagnetic technique, wherein electric resistivity or electric potential differences at selected locations on said workpiece are measured while an electric resistivity distribution inside said workpiece is changed by heating, cooling, or heating and cooling a front surface of said workpiece, thereby increasing an electric resistivity of a front surface of the workpiece compared with a rear surface thereof, resulting in increasing currents supplied on the rear surface side compared with the front surface.

2. The non-destructive inspection method of claim 1, which comprises locally heating, cooling, or heating and cooling a front surface of said workpiece.

3. A non-destructive inspection method for evaluating a rear surface flaw, an embedded flaw, or a material characteristic of a workpiece using a DC potential difference method, wherein an inspection sensitivity to the rear surface flaw, the embedded flaw, or the material characteristic is increased by changing the electric resistivity distribution inside the workpiece by locally heating a front surface of the workpiece, thereby increasing an electric resistivity of the front surface of the workpiece compared with an electric resistivity of the rear surface thereof, resulting in increasing currents supplied on a rear surface side compared with a case without the front surface being heated, and measuring electric potential differences at selected locations on said front surface.

4. A non-destructive inspection apparatus for evaluating a rear surface plan, an embedded flaw, or a material characteristic of a workpiece, comprising a sensor including a mechanism for bringing electric current input/output terminals connected to a constant current source, and electric potential difference measuring terminals in uniform contact with a front surface of said workpiece, and a heat source for locally heating the front surface of the workpiece, to thereby change an electric resistivity distribution inside the workpiece, wherein a rear surface flaw, an embedded flaw, or a material characteristic may be detected based on a measured electric potential difference, and measuring electic resistivity differences at selected locations on said front surface.

* * * * *